(12) United States Patent
Kordosky

(10) Patent No.: US 6,242,625 B1
(45) Date of Patent: Jun. 5, 2001

(54) PROCESS FOR EXTRACTING COPPER VALUES FROM COPPER CONTAINING ORES

(75) Inventor: Gary A. Kordosky, Tucson, AZ (US)

(73) Assignee: Henkel Corporation, Gulph Mills, PA (US)

(*) Notice: Subject to any disclaimer, the term of this patent is extended or adjusted under 35 U.S.C. 154(b) by 0 days.

(21) Appl. No.: 09/409,356

(22) Filed: Sep. 30, 1999

(51) Int. Cl.[7] .............. C07F 1/08; B01D 11/00; C02F 1/42
(52) U.S. Cl. .............. 556/110; 556/113; 423/24; 423/27; 210/634; 210/688
(58) Field of Search ............... 423/24, 27; 210/634, 210/688; 556/113, 110

(56) References Cited

U.S. PATENT DOCUMENTS

| | | | |
|---|---|---|---|
| 3,224,873 | 12/1965 | Swanson | 75/101 |
| 3,428,449 | 2/1969 | Swanson | 75/117 |
| 3,655,347 * | 4/1972 | Mattison et al. | 23/312 |
| 3,939,203 * | 2/1976 | Mattison et al. | 260/566 A |
| 3,952,775 | 4/1976 | Ogata | 137/625.38 |
| 4,020,105 | 4/1977 | Ackerley et al. | 260/566 |
| 4,020,106 | 4/1977 | Ackerley et al. | 260/566 |
| 4,029,704 | 6/1977 | Anderson | 260/566 A |
| 4,039,404 * | 8/1977 | Richards et al. | 204/106 |
| 4,069,119 * | 1/1978 | Wong | 204/106 |
| 4,085,146 | 4/1978 | Beswick | 260/600 R |
| 4,142,952 * | 3/1979 | Dalton | 204/106 |
| 4,173,616 | 11/1979 | Koenders et al. | 423/24 |
| 4,336,231 * | 6/1982 | Dalton | 423/24 |
| 5,895,633 * | 4/1999 | King | 423/24 |
| 5,908,605 * | 6/1999 | Virnig et al. | 423/24 |
| 6,107,523 * | 8/2000 | Virnig et al. | 568/412 |
| 6,113,804 * | 9/2000 | Dalton et al. | 252/184 |

FOREIGN PATENT DOCUMENTS 1322532   7/1973 (GB).

* cited by examiner

Primary Examiner—Porfirio Nazario-Gonzalez
(74) Attorney, Agent, or Firm—John E. Drach; Henry E. Millson, Jr.

(57) ABSTRACT

In an acid leach copper extraction circuit for leaching copper values from copper ores using a water-immiscible organic solvent solution containing a copper extractant and an acid strip solution, the improvement wherein the stripped organic solvent solution is contacted with copper-free fresh aqueous acid to remove additional copper values therefrom, and then the resulting super stripped organic and the copper-containing aqueous acid are sent to the copper extraction circuit.

24 Claims, 2 Drawing Sheets

PROCESS FOR EXTRACTING COPPER VALUES FROM COPPER CONTAINING ORES

FIELD OF THE INVENTION

This invention relates to the extraction of copper values from copper- containing ores.

BACKGROUND OF THE INVENTION

In the recovery of metals from metal ores, it is of course highly desirable to recover as much of the metal as is economically feasible from the ore.

In typical copper solvent extraction circuits copper recovery is about 90% where all of the raffinate (stripped aqueous acid leach solution) is recycled back to the leaching step for leaching the copper values from the copper ore.

However, in some plants using a copper extraction circuit a raffinate bleed must be removed to control the build up of impurities or to recover some other valuable metal such as cobalt. There are also plants where some of the raffinate recycled to the leaching step is lost, e.g. in agitation leach plants.

In the above plants it is desirable and even essential to recover a very high percentage of copper from the raffinate bleed stream and/or the raffinate used in recycling.

Several methods have been proposed to accomplish this, but such methods, e.g., acid neutralization of the bleed stream or high organic phase to aqueous phase ratios are not economically feasible.

There is accordingly, a strong need for a simple and economical process for reducing the concentration of copper in the raffinate or in the raffinate bleed stream, especially where a high copper content is present in the copper-pregnant acid leach solution.

The present inventor has discovered such a process.

SUMMARY OF THE INVENTION

The present process relates to a copper extraction circuit for extracting copper values from copper ores in which the extraction circuit comprises an aqueous acid leach solution for leaching the copper values from the ore, a water immiscible organic solvent solution containing a copper extractant to extract the copper values from the aqueous leach solution, a concentrated aqueous acid strip solution for stripping the copper values from the organic solvent solution, and means for the recovery of the copper from the pregnant strip solution.

The present invention comprises contacting the stripped organic solvent solution, before recycling this solution back into the extraction circuit, with aqueous acid to remove additional copper values therefrom, and then adding the aqueous acid containing the additional copper values to the raffinate recycled to the leaching step, to the tankhouse as acid makeup, to the spent electrolyte solution used to strip copper from the loaded organic phase in the main copper SX circuit, or a portion thereof to two or more of the above solutions.

DETAILED DESCRIPTION OF THE INVENTION

Figure 1:
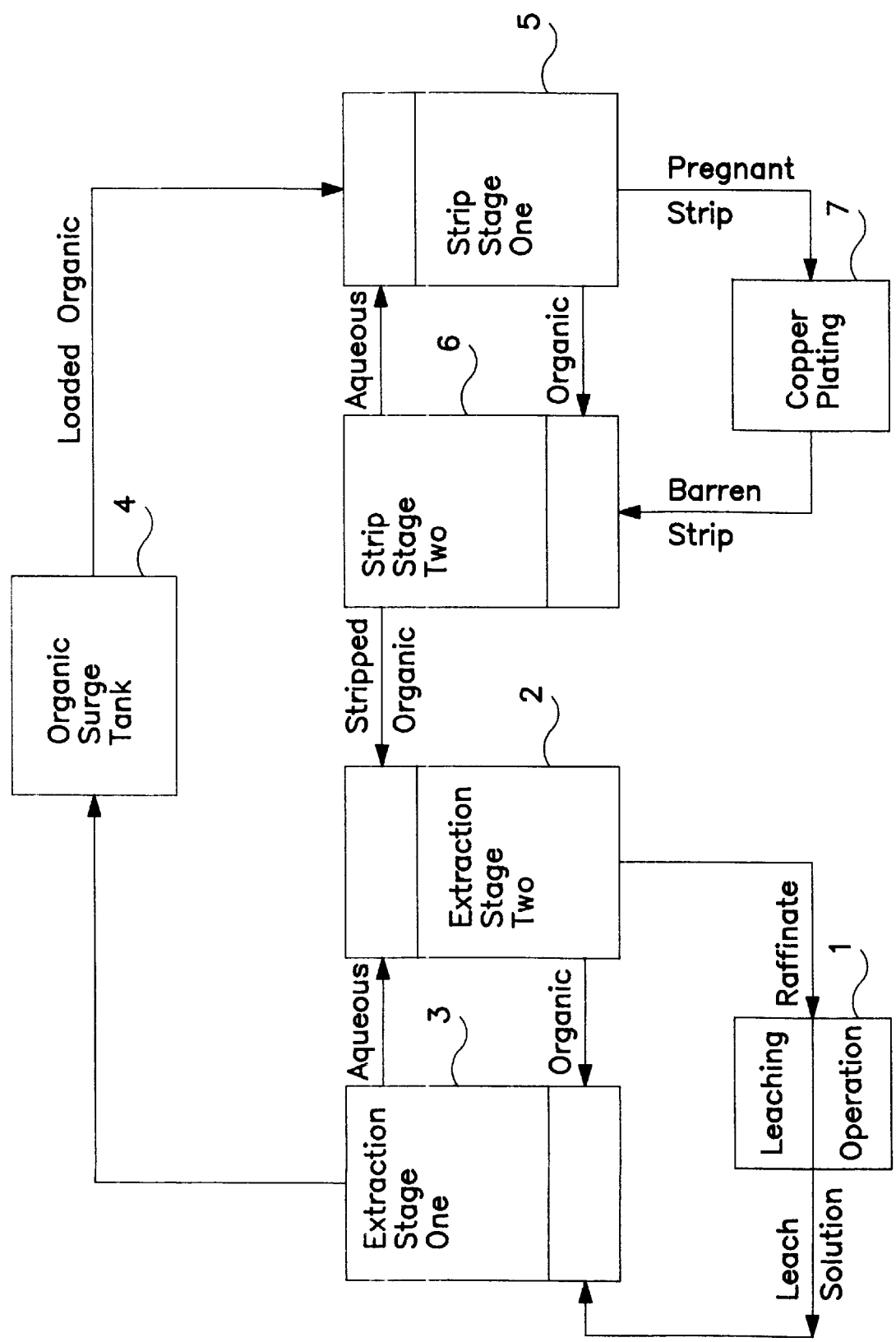
FIG. 1 is a schematic drawing of a typical copper leach, solvent extraction, electrowinning plant.

Other than in the operating examples, or where otherwise indicated, all numbers expressing quantities of ingredients or reaction conditions used herein are to be understood as modified in all instances by the term "about".

The solvent extraction process for extracting copper from copper ores typically involves the following steps:

1. Aqueous acid leaching of the copper ore to produce an aqueous acid leach solution containing copper ions and quantities of other metal ions. The aqueous leach acid solution dissolves salts of copper and other metals as it trickles through the ore. The metal values are usually leached with aqueous sulfuric acid, producing a leach solution having a pH of 0.9 to 2.0.

2. The copper-pregnant aqueous acid leach solution is mixed in tanks with an oxime extraction reagent which is dissolved in a water-immiscible organic solvent, e.g., a kerosene or other hydrocarbons. The reagent includes the oxime extractant which selectively forms a metal-extractant complex with the copper ions in preference to ions of other metals. The step of forming the complex is called the extraction or loading stage of the solvent extraction process.

3. The outlet of the mixer tanks continuously feeds to a large settling tank, where the organic solvent (organic phase), now containing the copper-extractant complex in solution, is separated from the depleted aqueous acid leach solution (aqueous phase). This part of the process is called phase separation. Usually, the process of extraction is repeated through two or more mixer/settler stages in counter current flow, in order to more completely extract the copper.

4. After extraction, the depleted aqueous acid leach solution (raffinate) is either discharged or recirculated to the ore body for further leaching.

5. The loaded organic phase containing the dissolved copper-extractant complex is fed to another set of mixer tanks, where it is mixed with an aqueous strip solution containing 150 to 200 g/L sulfuric acid and 30 to 35 g/L copper. The highly acid strip solution breaks apart the copper-extractant complex and permits the purified and concentrated copper to pass to the strip aqueous phase. This process of breaking the copper-extractant complex is called the stripping stage, and the stripping operation is often repeated through two mixer-settler stages in counter current flow to more completely strip the copper from the organic phase.

6. As in the extraction process described above (steps 2 and 3), the mixture is fed to another settler tank for phase separation.

7. From the stripping settler tank, the regenerated stripped organic phase is recycled to the extraction mixers to begin extraction again, and the copper is recovered from the strip aqueous phase, customarily by feeding the strip aqueous phase to an electrowinning tankhouse, where the copper metal values are deposited on plates by a process of electrodeposition. It is also possible to recover copper by crystallization of copper sulfate crystals.

8. After obtaining the copper values from the aqueous solution, the solution, known as spent electrolyte, is returned to the stripping mixers to begin stripping again.

In the present process, the stripped organic phase separated in step 6 is contacted with a highly-acid fresh aqueous acid, (super stripping stage) which is the same acid used in the extraction circuit, usually sulfuric acid, or other mineral acid, to reduce the copper content of the stripped organic phase to a significantly lower level, e.g. to 3 g/l or less, usually 2 g/l or less, to produce a "super stripped" organic phase which can extract considerably more copper than the stripped organic phase recycled to the extraction mixers in step 7. above. The fresh aqueous acid used to super strip the stripped organic phase, which is now a relatively high acid, low copper aqueous solution, can then be used as follows:

1) as acid makeup for leaching (step 1), or
2) as acid makeup to the tankhouse (step 7), or
3) as acid makeup to the strip solution entering the stripping stages of the copper solvent extraction circuit (steps 6 and 7), or
4) as acid makeup to a copper sulfate crystallization step if some or all of the final copper product is copper sulfate (step not shown).

The fresh aqueous acid used to super strip the stripped organic phase should have more than 200 g/L sulfuric acid and less than 30 g/L copper, e.g., at least 225 g/L sulfuric acid and 25 g/L copper or less.

Figure 2:
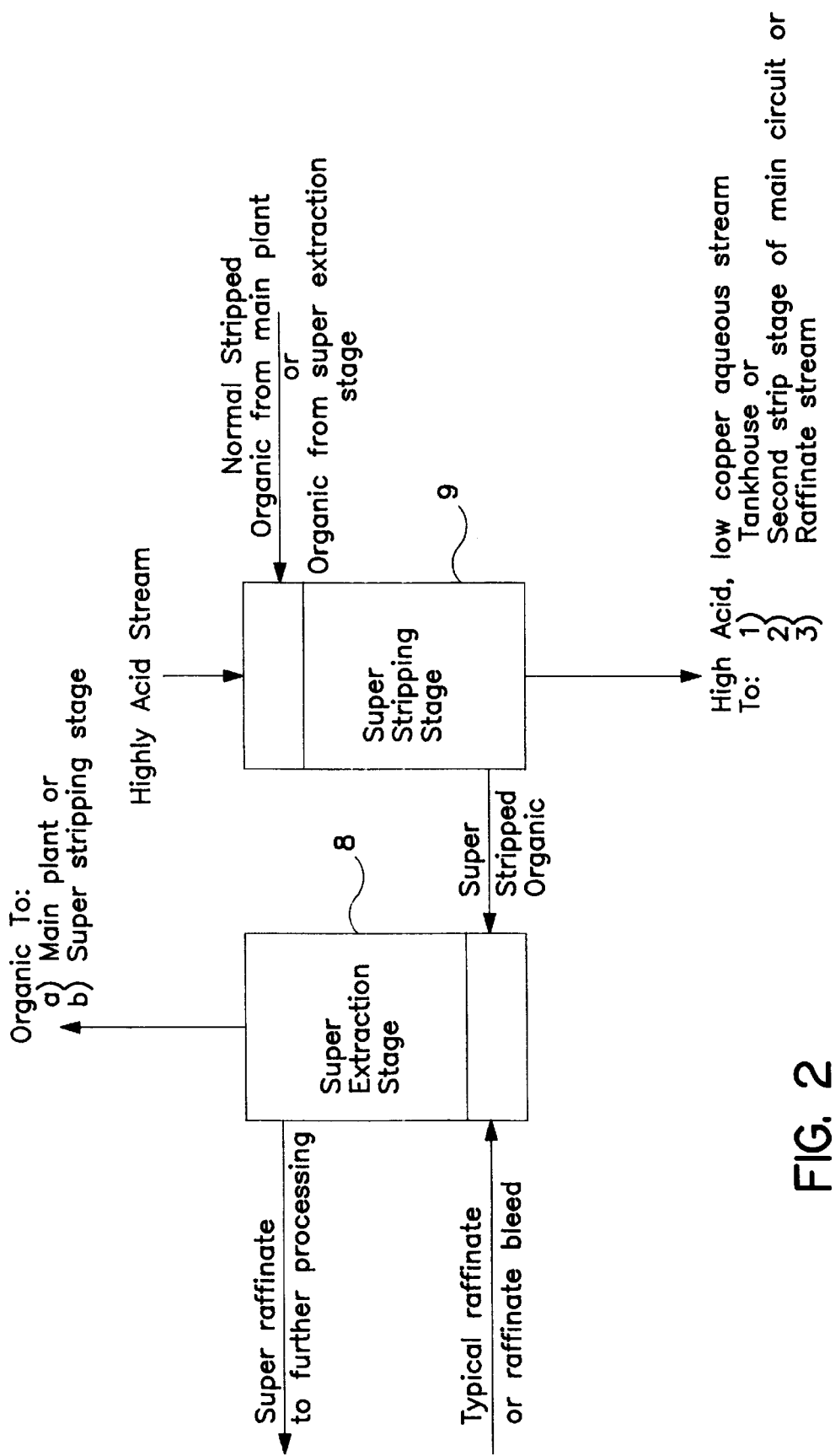
FIG. 2 is a schematic drawing of a copper leach, solvent extraction, electrowinning plant of the present invention.

The super stripped organic phase can then be used in step 2. and/or in the super extraction stage shown in FIG. 2.

The process of the invention is particularly useful where a high copper recovery is required, for example, where a raffinate bleed must be removed to control the buildup of impurities or to recover some other valuable metal such as cobalt, or where some of the raffinate recycled to the leaching step is lost, for example in agitation leach plants.

It should also be noted that the use of the super stripped organic phase in the present process also results in a "super raffinate", i.e. a raffinate having a much lower copper content than raffinates obtained in the typical solvent extraction process described above.

The copper extractants used most often in the process of the invention are oxime extractants of the hydroxy aryl ketone oxime type, the hydroxy aryl aldoxime type, or both types. A general formula for such oximes is given in formula I shown below:

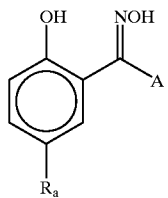

(I)

in which A can be:

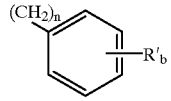

(i)

(ii) R''' or
(iii) H where R and R' can be individually alike or different and are saturated aliphatic groups of 1–25 carbon atoms, ethylenically unsaturated aliphatic groups of 3–25 carbon atoms or OR'' where R'' is a saturated or ethylenically unsaturated aliphatic group as defined above; n is 0 or 1; a and b are each 0, 1, 2, 3, or 4, with the proviso that both are not 0 and the total number of carbon atoms in $R_a$ and $R'_b$ is from 3 to 25, R''' is a saturated aliphatic group of 1–25 carbon atoms or an ethylenically unsaturated aliphatic group of 3 to 25 carbon atoms, with the proviso that the total number of carbon atoms in $R_a$ and R''' is from 3 to 25. Preferred compounds where A is (i) above are those in which a is 1, b is 0, R is a straight or branched chain alkyl group having from 7 to 12 carbon atoms and where R is attached in a position para to the hydroxyl group. Among those, the more preferred compounds are those wherein R''' is methyl and R and a are as designated. Compounds wherein n has a value of 0 (i.e. hydroxybenzophenone oxime compounds) can be prepared according to methods disclosed in Swanson U.S. Pat. Nos. 3,952,775 and 3,428,449. By reason of ready solubility in organic diluents commonly employed in solvent extraction and desirable properties of complexes of the compounds with copper, preferred benzophenone compounds are those having a single alkyl group of 7 to 12 carbon atoms in a position para to the hydroxyl group, in which the alkyl group is a mixture of isomers. Examples of such compounds are 2-hydroxy-5nonylbenzophenone oxime and 2-hydroxy-5-dodecylbenzophenone oxime, which are obtained as mixtures of the isomeric forms when commercial nonylphenol and dodecylphenol are respectively employed in their synthesis.

Compounds wherein n has a value of 1 (i.e. hydroxy phenyl benzyl ketone oxime compounds) can be prepared according to methods described in Anderson U.S. Pat. No. 4,029,704. Preferred phenyl benzyl ketone oximes like the above noted benzophenone oximes are those having an isomeric mixture of 7 to 12 carbon alkyl groups as a single substituent on the ring para to the hydroxyl group. These preferred compounds are exemplified by the compound, 2-hydroxy-5-nonylphenyl benzyl ketone oxime, as manufactured from a commercial nonylphenol comprising a mixture of nonyl isomeric forms.

Compounds of the hydroxy phenyl alkyl ketone oxime type can be prepared according to the procedures disclosed in UK Patent 1,322,532, and are especially preferred for use herein. As noted with regard to the benzophenone and phenyl benzyl ketone compounds described above, the preferred compounds of this type are also those having an isomeric mixture of 7 to 12 carbon alkyl groups as a single substituent on the ring para to the hydroxyl group. Also preferred are those in which the R''' alkyl group is methyl. Illustrative of such preferred compounds where A is $CH_3$ is 2-hydroxy-5-nonylphenyl methyl ketone oxime manufactured through the use of commercial nonylphenol.

Hydroxy aryl aldoxime extractants which can be employed alone or in mixtures with ketoximes are those in which A is H. These hydroxy benzaldoximes (also called "salicylaldoximes"), can be prepared according to methods described in Ackerley et al. U.S. Pat. Nos. 4,020,105 or 4,020,106 or by oximation of aldehydes prepared according to Beswick U.S. Pat. No. 4,085,146. Again preferred compounds are those having an isomeric mixture of isomeric 7 to 12 carbon alkyl groups as a single substituent para to the hydroxyl group, mixed alkyl isomeric forms of 2-hydroxy-5-heptyl benzaldoxime, 2-hydroxy-5-octyl benzaldoxime, 2-hydroxy-5-nonyl benzaldoxime and 2-hydroxy-5-dodecyl benzaldoxime are preferred, the most preferred for the purpose of the present invention where A is H is the dodecyl compound, i.e. 2-hydroxy-5-dodecyl benzaldoxime.

The oxime extractants in the above process can be used in conjunction with modifiers such as one or more equilibrium modifiers, and kinetic active substances. Equilibrium modifiers include long chain aliphatic alcohols such as n-hexanol, 2-ethylhexanol, isodecanol, dodecanol, tridecanol, hexadecanol and octadecanol; long chain alkylphenols such as heptylphenol, octylphenol, nonylphenol and dodecylphenol; organophosphorus compounds such as triloweralkyl ($C_4$ to $C_8$) phosphates, especially, tributyl phosphate and tri(2-ethylhexyl)phosphate; and either saturated or unsaturated aliphatic or aromatic-aliphatic esters containing from 10 to 30 carbon atoms, ketones, nitrates, ethers, amides, carbamates, carbonates, and the like. Kinetic active substances include α,β-hydroxy oximes described in Swanson, U.S. Pat. No. 3,224,873 and α,β-dioximes described in Koenders et al., U.S. Pat. No. 4,173,616.

The water-immiscible organic solvents used in the solvent extraction process of the invention are usually water-immiscible liquid hydrocarbon solvents. These include aliphatic and aromatic hydrocarbon diluents such as kerosene, benzene, toluene, xylene and the like. A choice of essentially water-immiscible hydrocarbon solvents or mixtures thereof will depend on various factors, including the plant design of the solvent extraction plant (mixer-settler units, extractors), and the like. The preferred solvents for use in the present invention are the aliphatic or aromatic hydrocarbons having flash points of 130° Fahrenheit and higher, preferably at least 150° and solubilities in water of less than 0.1% by weight. The solvents are essentially chemically inert. Representative commercially available solvents are ESCAID™ 100 and 110 (available from Exxon-Europe) having a flash point of 180° Fahrenheit; NORPAR™ 12 (available from Exxon-USA) with a flash point of 170° Fahrenheit; CONOCO™ C1214 (available from Conoco) with a flash point of 160° Fahrenheit and C 170 exempt solvent having a flash point above 150° Fahrenheit; and Aromatic 150 (an aromatic kerosene available from Exxon-USA having a flash point of 150° Fahrenheit), and other various kerosene and petroleum fractions available from other oil companies, such as the ORFORM™ SX series of solvent extraction diluents (available from Phillips 66: SX 1, 7, 11 and 12 each having a flash point above 150° Fahrenheit varying up to 215° Fahrenheit); and ESCAID™ series of hydrocarbon diluents (available from Exxon: 100, 110, 115, 120, 200 and 300, each having a flash point above 150° Fahrenheit; and EXXOL™ D80 solvent (also available from Exxon and having a flash point above 150° Fahrenheit).

In the process, the volume ratios of organic to aqueous (O:A) phase will vary widely since the contacting of any quantity of the oxime organic solution with the copper-containing aqueous solution will result in the extraction of copper values into the organic phase. For commercial practicality however, the organic (O) to aqueous (A) phase ratios for extraction are preferably in the range of about 20:1 to 1:20. It is desirable to maintain an effective O:A ratio of about 1:1 in the mixer unit by recycle of one of the streams. In the stripping step, the organic:aqueous stripping medium phase will preferably be in the range of about 1:4 to 20:1. For practical purposes, the extracting and stripping are normally conducted at ambient temperatures and pressure although higher and lower temperatures and pressures are entirely operable although higher temperatures will increase oxime degradation. While the entire operation can be carried out as a batch operation, most advantageously the process is carried out continuously with the various streams or solutions being recycled to the various operations in the process for recovery of the copper metal, including the leaching, extraction and the stripping steps.

In the extraction process, the organic solvent solutions contain the oxime extractant typically in an amount of about 2 to 15 weight/volume %, but higher or lower quantities can be used depending on the particular system.

After stripping of the copper values from the organic phase by the aqueous stripping solution and separation of the organic and aqueous stripping phase, the copper metal can be recovered by conventional recovery processes including, but not limited to, precipitation and electrowinning. Electrowinning is typically the preferred means of recovery of the copper from typical aqueous strip solutions containing 100 to 200 g/L sulfuric acid and 30 to 55 g/L copper.

Prior to stripping, it is not unusual to wash the organic phase, particularly where trace metals may be loaded on the organic extractant. One or more wash stages may accordingly be employed depending on any trace metals present, the amount of entrainment and the required purity of the final copper loaded stripping solution.

FIG. 1 is a schematic drawing of a typical copper solvent extractant circuit having two countercurrent stages of extraction and two countercurrent stages of stripping in combination with copper leaching and copper recovery by electrowinning.

The leaching stage (1) is carried out by leaching the copper ore with the raffinate from a second extraction stage (2) of the circuit. The copper-pregnant leach solution is sent to a first extraction stage (3) where it is contacted with the partially loaded organic phase from second extraction stage (2). The raffinate from first extraction stage (3) is sent to second extraction stage (2), and the copper-loaded organic phase is sent to organic surge tank (4), and then to a first strip stage (5) where it is contacted with aqueous strip solution from a second strip stage (6). The resulting copper-pregnant aqueous strip solution from first strip stage (5) is sent to an electrowinning plant (7). The stripped organic phase from first strip stage (5) is sent to second strip stage (6). The spent electrolyte from the electrowinning plant (7) is sent to the second strip stage (6). The stripped organic from the second strip stage (6) is sent to the second extraction stage (2).

FIG. 2 is a schematic drawing of the process of the invention.

Stripped organic phase from the main plant (e.g. from the second strip stage (6) of FIG. 1) or the organic phase from super extraction stage (8) is introduced into super stripping stage (9), where the organic phase is contacted with fresh aqueous acid. The aqueous acid containing copper values is sent to the tankhouse (electrowinning plant (7) in FIG. 1) as acid makeup, or the second strip stage in the main circuit (second strip stage (6) in FIG. 1) or a raffinate stream (entering leaching stage (1) in FIG. 1). The super stripped organic phase from super stripping stage (9) is sent to super extraction stage (8). The raffinate from the main circuit (e.g. from extraction stage (2) in FIG. 1) or a raffinate bleed stream therefrom is passed into super extraction stage (8). The resulting super raffinate is then sent to further processing for recovery of some other metal, to waste treatment, or to some other process. The organic phase from super extraction stage (8) is sent to the main circuit (e.g. first strip stage (5) in FIG. 1) or to super stripping stage (9).

The invention will be illustrated but not limited by the following examples.

EXAMPLES

Example 1

About one liter of solution containing 30 volume % LIX® 622N in ESCAID™ 100, a typical high flash point hydrocarbon diluent used in copper solvent extraction, was prepared. LIX® 622N is a commercially available copper solvent extraction reagent containing 5-nonyl salicylaldoxime and tridecyl alcohol. A volume of this solution was contacted for three minutes in a separatory funnel with an equal volume of an aqueous solution containing 6 g/l Cu and a pH of 2 such that about 5 g/l of Cu is extracted into the organic phase. The resulting organic phase was then contacted three separate times for three minutes each contact with an equal volume of a typical aqueous strip solution exiting the second strip stage in two stages of stripping. This typical aqueous strip solution contains 39.3 g/l copper and 167.7 g/l sulfuric acid. The resulting organic solution contained 5.92 g/l Cu and is representative of a stripped organic exiting the stripping section of a typical, two strip stage copper solvent extraction plant when 30 volume % LIX® 622N is the extractant. This typical stripped organic was then vigorously contacted at various organic to aqueous ratios with a copper leach solution containing 21.2 g/l copper and a pH of 1.8 for sufficient time to attain equilibrium, normally 5 to 10 minutes. After the phases were separated the resulting aqueous and organic phases were analyzed for copper. The analytical data is given in Table 1 below:

TABLE 1

| Organic/Aqueous | g/l Cu | |
|---|---|---|
| Ratio | Organic | Aqueous |
| 10/1 | 7.87 | 1.62 |
| 5/1 | 9.63 | 2.45 |
| 3/1 | 11.6 | 4.02 |
| 3/2 | 14.4 | 8.34 |
| 1/1 | 15.5 | 11.5 |
| 2/3 | 16.2 | 14.1 |
| 1/3 | 17.0 | 17.2 |
| 1/5 | 17.2 | 18.6 |
| 1/10 | 17.5 | 19.9 |

Using the data from Table 1 above a computer generated material mass balance McCabe-Thiele diagram for a two extraction stage, two strip stage circuit assuming 95% stage efficiency shows that at an organic to aqueous advance flow ratio of 2.45 a raffinate of 2.14 g/l copper can be achieved (90% copper recovery). Three stages of copper solvent extraction coupled with two stages of strip would give a copper recovery of 93.8% under the same conditions. Three extraction stages represent a practical limit on staging for copper solvent extraction plants, therefore, 93.8% copper extraction represents a practical limit of copper recovery for the above copper leach solution.

In order to simulate solvent extraction of a bleed stream where a very high copper recovery is desired the following experiments were carried out. A sample of normal stripped organic having 6.30 g/l Cu was vigorously contacted at an organic/aqueous ratio of 1 for five minutes with an aqueous solution having 5 g/l Cu and 218 g/l $H_2SO_4$ to produce a super stripped organic having 1.43 g/l Cu. A small sample was retained for analysis and then the super stripped organic was vigorously contacted at an organic/aqueous ratio of 1 for five minutes with a sample of normal raffinate which was produced by extracting 90% of the copper from the above copper leach solution. After the phases separated the resulting aqueous phase, termed S.S. raffinate (1) was analyzed for copper.

Another sample of normal stripped organic with 6.3 g/l Cu was contacted at an organic/aqueous ratio of 1 for five minutes with an aqueous solution having 226 g/l $H_2SO_4$ and no copper to give a super stripped organic of 0.76 g/l Cu. This super stripped organic was then contacted with a sample of normal raffinate as described directly above. In this sample the final aqueous phase was called S.S. raffinate (2).

The results are given in Table 2 below:

TABLE 2

| Extraction Using Super Stripped LIX ® 622N | | | | |
|---|---|---|---|---|
| Strip Aqueous | 5 g/l Cu, 218 g/l $H_2SO_4$ | | 226 g/l $H_2SO_4$ | |
| Sample | g/l Cu | Cu Recovery | g/l Cu | Cu Recovery |
| Normal stripped organic | 6.30 | | 6.30 | |
| Super stripped organic | 1.43 | | 0.76 | |
| Normal raffinate | 2.15 | 90.0% | 2.15 | 90.0% |
| S.S. raffinates (1) & (2) | 0.400 | 98.1% | 0.322 | 98.5% |

It can be seen from the above table that a very high copper extraction was obtained, greater than 98% in both samples. Thus the desired very high copper recovery for the bleed stream was achieved.

Example 2

The process of Example 1 was repeated except that the organic phase was a 30 volume % solution of LIX® 860-I also a commercially available copper solvent extraction reagent containing 5-nonyl salicylaldoxime in a high flash point hydrocarbon diluent. The results are given in Table 3 below:

TABLE 3

| Organic/Aqueous | g/l Cu | |
|---|---|---|
| Ratio | Organic | Aqueous |
| 10/1 | 11.1 | 1.61 |
| 5/1 | 12.8 | 2.61 |
| 3/1 | 14.6 | 4.66 |
| 3/2 | 16.4 | 10.3 |
| 1/1 | 16.9 | 13.7 |
| 2/3 | 17.2 | 16.2 |
| 1/3 | 17.6 | 18.5 |
| 1/5 | 17.7 | 20.0 |
| 1/10 | 17.9 | 20.7 |

In this example a computer generated material mass balance McCabe-Thiele diagram for a two extraction stage, two strip stage circuit assuming 95% stage efficiency shows that at an organic to aqueous advance flow ratio of 2.86 a raffinate of 2.14 g/l copper can be achieved (90% copper recovery).

Super stripped organic phases were prepared as described in Example 1. These super stripped organics were then used to generate super stripped raffinates also as described in Example 1. The results are given in Table 4 below:

TABLE 4

| | 5 g/l Cu, | | | |
|---|---|---|---|---|
| Strip Aqueous | 218 g/l $H_2SO_4$ | | 226 g/l $H_2SO_4$ | |
| Sample | g/l Cu | Cu Recovery | g/l Cu | Cu Recovery |
| Normal stripped organic | 9.14 | | 9.14 | |
| Super stripped organic | 3.02 | | 2.39 | |
| Normal raffinate | 2.13 | 90.0% | 2.13 | 90.0% |
| S.S. raffinates (1) & (2) | 0.336 | 98.4% | 0.246 | 98.8% |

As in Example 1, a very high percentage of copper extraction was obtained, greater than 98%, when a super stripped organic phase was employed.

What is claimed is:

1. A process for reducing the copper content of an acid stripped water-immiscible, organic solvent solution containing a copper extractant and residual copper values comprising contacting the stripped organic solvent solution with an aqueous acid solution which can further reduce the copper content of the stripped organic solvent solution.

2. The process of claim 1 wherein the aqueous acid solution is aqueous sulfuric acid.

3. The process of claim 1 wherein the aqueous acid solution is copper free.

4. The process of claim 1 wherein the aqueous acid solution comprises more than about 200 g/L sulfuric acid and less than about 30 g/L copper.

5. The process of claim 1 wherein the super stripped organic solvent solution and the aqueous acid used to produce the super stripped organic solvent solution are sent to an acid leach copper ore extraction circuit.

6. The process of claim 5 wherein the aqueous acid containing copper values is added to at least one of an aqueous acid leach solution, an aqueous acid strip solution, or a spent electrolyte solution in the acid leach copper ore extraction circuit.

7. The process of claim 1 wherein the copper extractant comprises an hydroxy aryl ketone oxime.

8. The process of claim 1 wherein the copper extractant comprises an hydroxy aryl aldoxime.

9. The process of claim 1 wherein the concentration of acid in the copper-free aqueous acid is greater than the concentration of acid used to strip the organic solvent solution.

10. In a process for the extraction of copper from a copper ore in a copper extraction circuit in which the ore is extracted with an aqueous acid leach solution, the aqueous acid leach solution is contacted with a water-immiscible organic solvent solution containing a copper extractant to extract copper from the aqueous acid leach solution, the copper-pregnant organic solvent solution is stripped with an aqueous acid stripping solution, and the copper is removed from the resulting copper-pregnant aqueous stripping solution, resulting in a spent electrolyte solution, the improvement wherein the stripped organic solvent solution is contacted with an aqueous acid solution to remove additional copper values therefrom to form a super stripped organic solvent solution.

11. The process of claim 10 wherein the super stripped organic solvent solution and the aqueous acid solution used to produce the super stripped organic solvent solution are sent to the copper extraction circuit.

12. The process of claim 11 wherein said aqueous acid solution is added to at least one of the aqueous acid leach solution, the aqueous acid stripping solution, or the spent electrolyte solution.

13. The process of claim 10 wherein the aqueous acid is a mineral acid.

14. The process of claim 13 wherein the mineral acid is sulfuric acid.

15. The process of claim 10 wherein the aqueous acid solution comprises more than about 200 g/L sulfuric acid and less than about 30 g/L copper.

16. The process of claim 10 wherein the copper extractant comprises an hydroxy aryl ketone oxime.

17. The process of claim 10 wherein the copper extractant comprises an hydroxy aryl aldoxime.

18. The process of claim 10 wherein the concentration of acid in the copper-free aqueous acid is greater than the concentration of acid used to strip the copper-pregnant organic solvent solution.

19. A solvent extraction process for extracting copper from a copper ore comprising the steps of A) leaching the copper ore with an aqueous acid to produce an aqueous acid leach solution containing copper ions;

B) mixing the aqueous acid leach solution from step A) with an oxime extractant reagent dissolved in a water-immiscible organic solvent to form an organic solvent solution of a metal-extractant complex with the copper ions;

C) separating the resulting organic solvent solution from the now depleted aqueous acid leach solution;

D) contacting the organic solvent solution with a highly acid aqueous strip solution to strip the copper from the metal-extractant complex in the organic solvent;

E) contacting the stripped organic solvent from step D) with an aqueous acid which is more highly acidic than the highly acid aqueous strip solution used in step D) to further reduce the copper content of the stripped organic solvent;

F) recovering copper from the highly acid aqueous copper-containing strip solution from step D);

G) returning the copper-depleted aqueous acid strip solution from step F) to step D).

20. The process of claim 19 wherein the aqueous acid from step F) is used as one or more of a) acid makeup for the aqueous acid leach solution used in step A), b) as acid makeup for the copper-containing aqueous acid strip solution in step F), or c) as acid makeup for the aqueous acid strip solution used in step D).

21. The process of claim 19 wherein the further stripped organic solvent from step E) is used in step B).

22. The process of claim 19 wherein the highly acid aqueous strip solution in step D) contains from about 150 to about 200 g/L sulfuric acid, and the aqueous acid used in step E) contains more than 200 g/L sulfuric acid.

23. The process of claim 22 wherein the aqueous acid used in step E) contains at least 225 g/L sulfuric acid.

24. The process of claim 19 wherein in step B) the oxime extractant reagent is a hydroxy aryl ketone oxime, a hydroxy aryl aldoxime, or a mixture thereof.

* * * * *